United States Patent
Payne et al.

(10) Patent No.: US 9,221,890 B2
(45) Date of Patent: Dec. 29, 2015

(54) GIGAXONIN FUSION PROTEIN AND METHODS FOR TREATING GIANT AXONAL NEUROPATHY

(71) Applicant: Indiana University Research and Technology Corporation, Indianapolis, IN (US)

(72) Inventors: R. Mark Payne, Zionsville, IN (US); Clifford M. Babbey, Indianapolis, IN (US); Kyle B. Martin, Indianapolis, IN (US); Samuel M. Beard, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/354,150

(22) PCT Filed: Oct. 25, 2012

(86) PCT No.: PCT/US2012/061979
§ 371 (c)(1),
(2) Date: Apr. 25, 2014

(87) PCT Pub. No.: WO2013/063309
PCT Pub. Date: May 2, 2013

(65) Prior Publication Data
US 2014/0336128 A1 Nov. 13, 2014

Related U.S. Application Data

(60) Provisional application No. 61/550,940, filed on Oct. 25, 2011.

(51) Int. Cl.
*A61K 39/00* (2006.01)
*A61K 39/385* (2006.01)
*C07K 14/47* (2006.01)
*A61K 38/00* (2006.01)

(52) U.S. Cl.
CPC .............. *C07K 14/47* (2013.01); *A61K 38/00* (2013.01); *C07K 2319/10* (2013.01)

(58) Field of Classification Search
None
See application file for complete search history.

(56) References Cited

U.S. PATENT DOCUMENTS 5,569,648 A 10/1996 Lewis et al.
2006/0063152 A1 3/2006 Ohara et al.

OTHER PUBLICATIONS

Wang et al., Current Biol., 2005, 15:2050-5.*
Mark Payne et al., "Cardiomyopathy of Friedrich's Ataxia: Use of Mouse Models to Understand Human Disease and Guide Therapeutic Development," Pediatric Cardiology, Springer-Verlag, US, vol. 32, No. 3, Mar. 1, 2011, pp. 366-378.
Silke Mussche et al., "Proteomic analysis in giant axonal neuropathy: New insights into disease mechanisms," Muscle & Nerve, vol. 46, No. 2, Jul. 16, 2012, pp. 246-256.
J. Ding, "Microtubule-associated protein 1B: a neuronal binding partner for gigaxonin," The Journal of Cell Biology, vol. 158, No. 3, Jul. 29, 2002, pp. 427-433.
Supplemental European Search Report received in EP Patent Application No. 12843112.9, mailed Feb. 12, 2015.
Bomont, P. et al., "The gene encoding gigaxonin, a new member of the cytoskeletal BTB/kelch repeat family, is mutated in giant axonal neuropathy", Nature Genetics, Nov. 2000, vol. 26, No. 3, pp. 370-374.
Yang, Y. et al., "Giant axonal neuropathy", Cellular and Molecular Life Sciences, Mar. 2007, vol. 64, No. 5, pp. 601-609.
Cullen, V. C. et al., "Gigaxonin is associated with the Golgi and dimerises via its BTB domain", Neuroreport, Apr. 9, 2004, vol. 15, No. 5, pp. 873-876.
Lamb N., et al., "Modulation of vimentin containing intermediate filament distribution and phosphorylation in living fibroblasts by the cAMP-dependent protein kinase.", pp. 2409-2422, J Cell Biol. 1989.
Wadia J. and Dowdy S., "Protein Transduction Technology," Curr Opin Biotechnol. 2002, 13:52-56.
International Search Report and Written Opinion, PCT/US2012/061979, dated Feb. 27, 2013 (12 pages).
International Preliminary Report on Patentability, PCT/US2012/061979, dated May 8, 2014 (7 pages).

* cited by examiner

*Primary Examiner* — Olga N Chernyshev
(74) *Attorney, Agent, or Firm* — Stinson Leonard Street LLP

(57) ABSTRACT

The present disclosure relates generally to fusion proteins including gigaxonin coupled to a cell penetrant peptide. These fusion proteins can be used to treat GAN in a subject in need thereof. Administration of the fusion proteins allows for control of at least one of Galectin-1 (GAL-1) levels and phosphorylated vimentin protein levels, thereby mediating aggregation of vimentin and the formation of vimentin-free zones in cells.

5 Claims, 17 Drawing Sheets

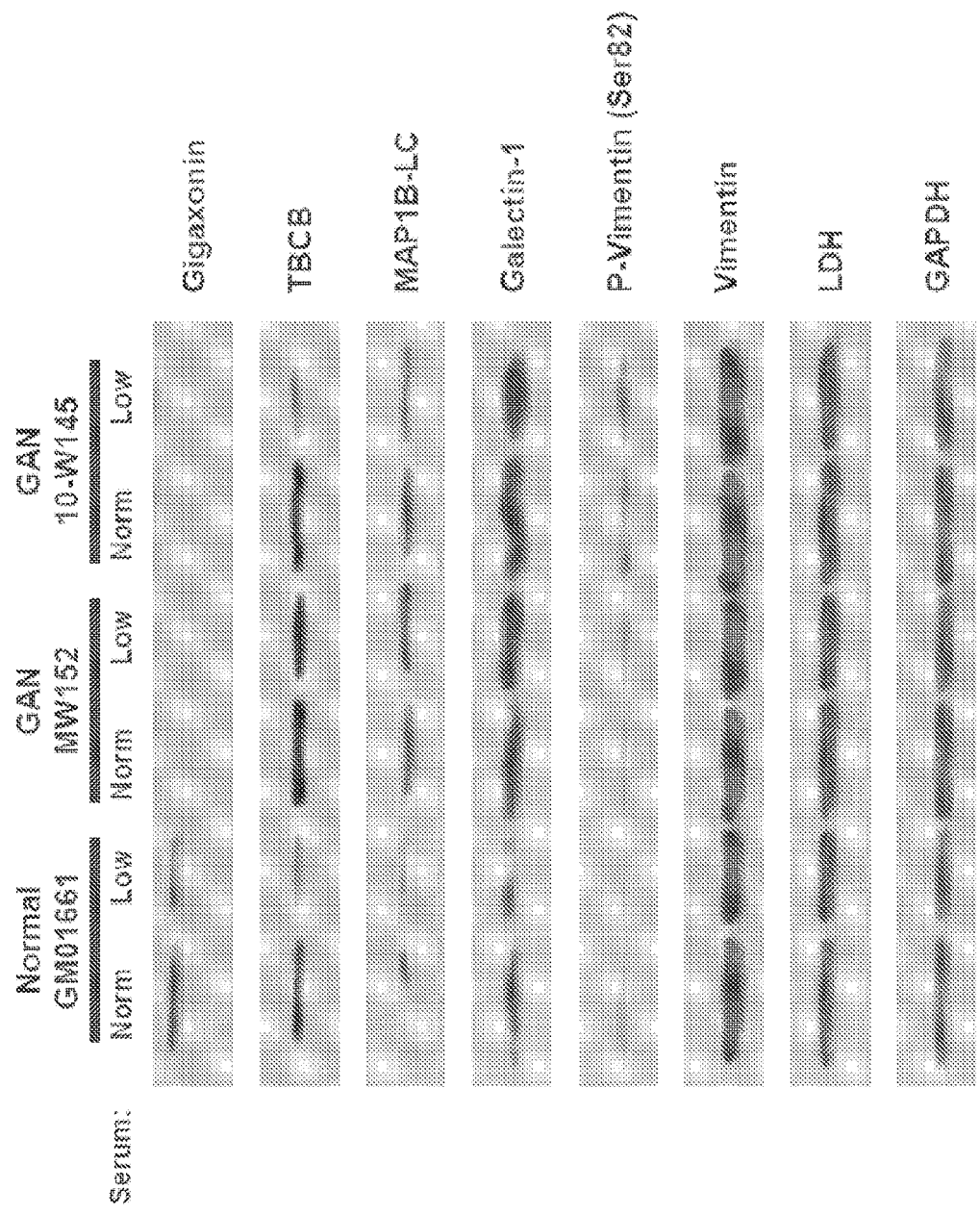

VIMENTIN

TUBULIN

VIMENTIN

TUBILIN

VIMENTIN

VIMENTIN

TUBULIN

TUBULIN

NORMAL
VIMENTIN/TUBULIN OVERLAY

VIMENTIN

TUBULIN

GAN PATIENT
VIMENTIN/TUBULIN OVERLAY

VIMENTIN

TUBULIN

TREATED GAN PATIENT
VIMENTIN/TUBULIN OVERLAY

VIMENTIN

TUBULIN

UNTREATED GAN PATIENT
VIMENTIN/TUBULIN OVERLAY

VIMENTIN

TUBULIN

TREATED GAN PATIENT
VIMENTIN/TUBULIN OVERLAY

VIMENTIN

TUBULIN

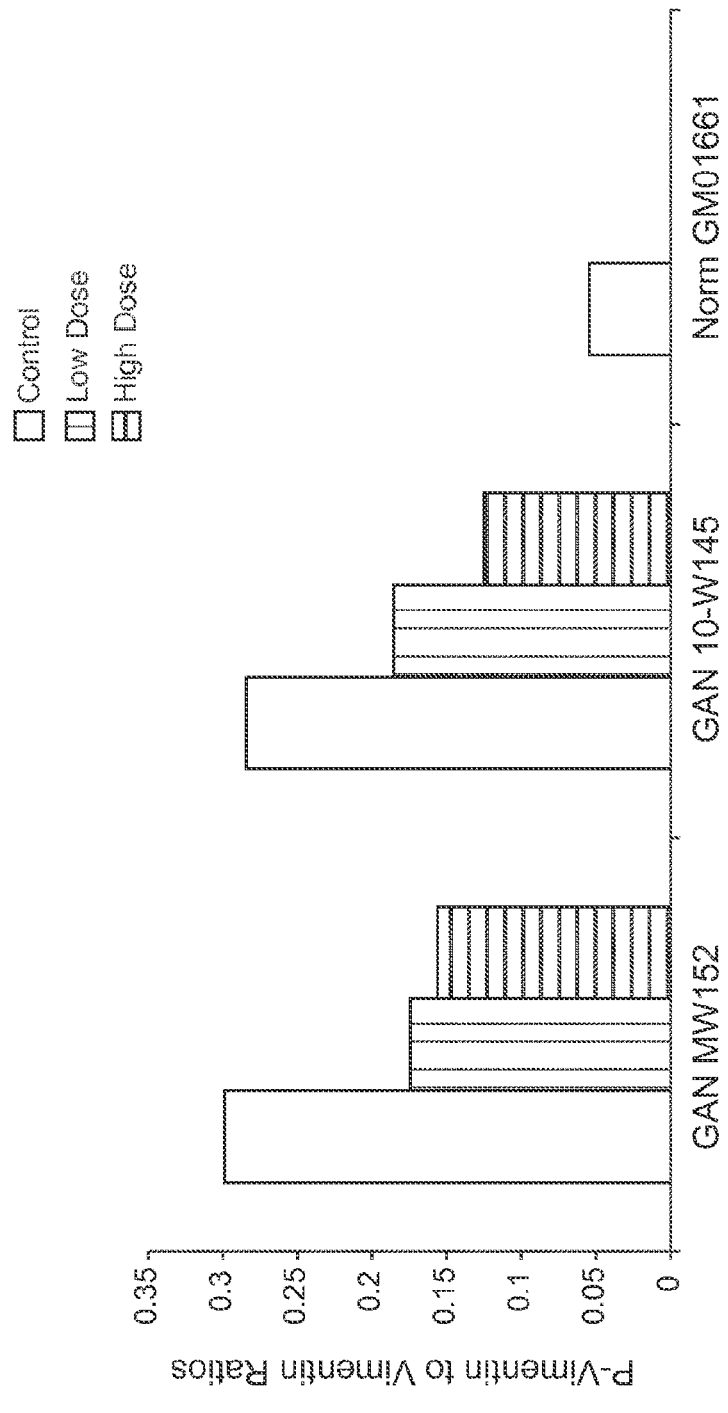

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Tyr Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Tyr Ala Arg Ala Ala Ala Arg Gln Ala Arg Ala
1               5                   10

<210> SEQ ID NO 3
<211> LENGTH: 21
<212> TYPE: PRT
<213> ORGANISM: Artificial Sequence
```

```
<220> FEATURE:
<223> OTHER INFORMATION: Synthetic

<400> SEQUENCE: 3

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 4
<211> LENGTH: 27
<212> TYPE: PRT
<213> ORGANISM: Artificial Sequence
<220> FEATURE:
<223> OTHER INFORMATION: Synthetic

<400> SEQUENCE: 4

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 34
<212> TYPE: PRT
<213> ORGANISM: Artificial Sequence
<220> FEATURE:
<223> OTHER INFORMATION: Synthetic

<400> SEQUENCE: 6

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Arg Arg Arg Arg Arg Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic
```

-continued

<400> SEQUENCE: 8

Arg Arg Arg Arg Arg Arg Arg Arg
1               5

<210> SEQ ID NO 9
<211> LENGTH: 597
<212> TYPE: PRT
<213> ORGANISM: Homo sapiens

<400> SEQUENCE: 9

Met Ala Glu Gly Ser Ala Val Ser Asp Pro Gln His Ala Ala Arg Leu
1               5                   10                  15

Leu Arg Ala Leu Ser Ser Phe Arg Glu Ser Arg Phe Cys Asp Ala
            20                  25                  30

His Leu Val Leu Asp Gly Glu Glu Ile Pro Val Gln Lys Asn Ile Leu
            35                  40                  45

Ala Ala Ala Ser Pro Tyr Ile Arg Thr Lys Leu Asn Tyr Asn Pro Pro
    50                  55                  60

Lys Asp Asp Gly Ser Thr Tyr Lys Ile Glu Leu Gly Ile Ser Val
65                  70                  75                  80

Met Val Met Arg Glu Ile Leu Asp Tyr Ile Phe Ser Gly Gln Ile Arg
                85                  90                  95

Leu Asn Glu Asp Thr Ile Gln Asp Val Val Gln Ala Ala Asp Leu Leu
            100                 105                 110

Leu Leu Thr Asp Leu Lys Thr Leu Cys Cys Glu Phe Leu Glu Gly Cys
        115                 120                 125

Ile Ala Ala Glu Asn Cys Ile Gly Ile Arg Asp Phe Ala Leu His Tyr
130                 135                 140

Cys Leu His His Val His Tyr Leu Ala Thr Glu Tyr Leu Glu Thr His
145                 150                 155                 160

Phe Arg Asp Val Ser Ser Thr Glu Glu Phe Leu Glu Leu Ser Pro Gln
                165                 170                 175

Lys Leu Lys Glu Val Ile Ser Leu Glu Lys Leu Asn Val Gly Asn Glu
            180                 185                 190

Arg Tyr Val Phe Glu Ala Val Ile Arg Trp Ile Ala His Asp Thr Glu
        195                 200                 205

Ile Arg Lys Val His Met Lys Asp Val Met Ser Ala Leu Trp Val Ser
210                 215                 220

Gly Leu Asp Ser Ser Tyr Leu Arg Glu Gln Met Leu Asn Glu Pro Leu
225                 230                 235                 240

Val Arg Glu Ile Val Lys Glu Cys Ser Asn Ile Pro Leu Ser Gln Pro
                245                 250                 255

Gln Gln Gly Glu Ala Met Leu Ala Asn Phe Lys Pro Arg Gly Tyr Ser
            260                 265                 270

Glu Cys Ile Val Thr Val Gly Gly Glu Glu Arg Val Ser Arg Lys Pro
        275                 280                 285

Thr Ala Ala Met Arg Cys Met Cys Pro Leu Tyr Asp Pro Asn Arg Gln
290                 295                 300

Leu Trp Ile Glu Leu Ala Pro Leu Ser Met Pro Arg Ile Asn His Gly
305                 310                 315                 320

Val Leu Ser Ala Glu Gly Phe Leu Phe Val Phe Gly Gly Gln Asp Glu
                325                 330                 335

Asn Lys Gln Thr Leu Ser Ser Gly Glu Lys Tyr Asp Pro Asp Ala Asn
            340                 345                 350

Thr Trp Thr Ala Leu Pro Pro Met Asn Glu Ala Arg His Asn Phe Gly
            355                 360                 365

Ile Val Glu Ile Asp Gly Met Leu Tyr Ile Leu Gly Gly Glu Asp Gly
    370                 375                 380

Glu Lys Glu Leu Ile Ser Met Glu Cys Tyr Asp Ile Tyr Ser Lys Thr
385                 390                 395                 400

Trp Thr Lys Gln Pro Asp Leu Thr Met Val Arg Lys Ile Gly Cys Tyr
                405                 410                 415

Ala Ala Met Lys Lys Ile Tyr Ala Met Gly Gly Ser Tyr Gly
                420                 425                 430

Lys Leu Phe Glu Ser Val Glu Cys Tyr Asp Pro Arg Thr Gln Gln Trp
            435                 440                 445

Thr Ala Ile Cys Pro Leu Lys Glu Arg Arg Phe Gly Ala Val Ala Cys
            450                 455                 460

Gly Val Ala Met Glu Leu Tyr Val Phe Gly Gly Val Arg Ser Arg Glu
465                 470                 475                 480

Asp Ala Gln Gly Ser Glu Met Val Thr Cys Lys Ser Glu Phe Tyr His
                485                 490                 495

Asp Glu Phe Lys Arg Trp Ile Tyr Leu Asn Asp Gln Asn Leu Cys Ile
                500                 505                 510

Pro Ala Ser Ser Phe Val Tyr Gly Ala Val Pro Ile Gly Ala Ser
            515                 520                 525

Ile Tyr Val Ile Gly Asp Leu Asp Thr Gly Thr Asn Tyr Asp Tyr Val
    530                 535                 540

Arg Glu Phe Lys Arg Ser Thr Gly Thr Trp His His Thr Lys Pro Leu
545                 550                 555                 560

Leu Pro Ser Asp Leu Arg Arg Thr Gly Cys Ala Ala Leu Arg Ile Ala
                565                 570                 575

Asn Cys Lys Leu Phe Arg Leu Gln Leu Gln Gln Gly Leu Phe Arg Ile
                580                 585                 590

Arg Val His Ser Pro
            595

<210> SEQ ID NO 10
<211> LENGTH: 612
<212> TYPE: PRT
<213> ORGANISM: Artificial Sequence
<220> FEATURE:
<223> OTHER INFORMATION: Synthetic

<400> SEQUENCE: 10

Tyr Gly Arg Lys Lys Arg Arg Gln Arg Arg Gly Gly Ser Thr Met
1               5                   10                  15

Ala Glu Gly Ser Ala Val Ser Asp Pro Gln His Ala Ala Arg Leu Leu
                20                  25                  30

Arg Ala Leu Ser Ser Phe Arg Glu Glu Ser Arg Phe Cys Asp Ala His
            35                  40                  45

Leu Val Leu Asp Gly Glu Glu Ile Pro Val Gln Lys Asn Ile Leu Ala
        50                  55                  60

Ala Ala Ser Pro Tyr Ile Arg Thr Lys Leu Asn Tyr Asn Pro Pro Lys
65                  70                  75                  80

Asp Asp Gly Ser Thr Tyr Lys Ile Glu Leu Glu Gly Ile Ser Val Met
                85                  90                  95

Val Met Arg Glu Ile Leu Asp Tyr Ile Phe Ser Gly Gln Ile Arg Leu
                100                 105                 110

```
Asn Glu Asp Thr Ile Gln Asp Val Gln Ala Ala Asp Leu Leu Leu
            115                 120                 125

Leu Thr Asp Leu Lys Thr Leu Cys Cys Glu Phe Leu Glu Gly Cys Ile
    130                 135                 140

Ala Ala Glu Asn Cys Ile Gly Ile Arg Asp Phe Ala Leu His Tyr Cys
145                 150                 155                 160

Leu His His Val His Tyr Leu Ala Thr Glu Tyr Leu Glu Thr His Phe
                165                 170                 175

Arg Asp Val Ser Ser Thr Glu Glu Phe Leu Glu Leu Ser Pro Gln Lys
            180                 185                 190

Leu Lys Glu Val Ile Ser Leu Glu Lys Leu Asn Val Gly Asn Glu Arg
        195                 200                 205

Tyr Val Phe Glu Ala Val Ile Arg Trp Ile Ala His Asp Thr Glu Ile
    210                 215                 220

Arg Lys Val His Met Lys Asp Val Met Ser Ala Leu Trp Val Ser Gly
225                 230                 235                 240

Leu Asp Ser Ser Tyr Leu Arg Glu Gln Met Leu Asn Glu Pro Leu Val
                245                 250                 255

Arg Glu Ile Val Lys Glu Cys Ser Asn Ile Pro Leu Ser Gln Pro Gln
            260                 265                 270

Gln Gly Glu Ala Met Leu Ala Asn Phe Lys Pro Arg Gly Tyr Ser Glu
        275                 280                 285

Cys Ile Val Thr Val Gly Gly Glu Glu Arg Val Ser Arg Lys Pro Thr
    290                 295                 300

Ala Ala Met Arg Cys Met Cys Pro Leu Tyr Asp Pro Asn Arg Gln Leu
305                 310                 315                 320

Trp Ile Glu Leu Ala Pro Leu Ser Met Pro Arg Ile Asn His Gly Val
                325                 330                 335

Leu Ser Ala Glu Gly Phe Leu Phe Val Phe Gly Gly Gln Asp Glu Asn
            340                 345                 350

Lys Gln Thr Leu Ser Ser Gly Glu Lys Tyr Asp Pro Asp Ala Asn Thr
        355                 360                 365

Trp Thr Ala Leu Pro Pro Met Asn Glu Ala Arg His Asn Phe Gly Ile
    370                 375                 380

Val Glu Ile Asp Gly Met Leu Tyr Ile Leu Gly Gly Glu Asp Gly Glu
385                 390                 395                 400

Lys Glu Leu Ile Ser Met Glu Cys Tyr Asp Ile Tyr Ser Lys Thr Trp
                405                 410                 415

Thr Lys Gln Pro Asp Leu Thr Met Val Arg Lys Ile Gly Cys Tyr Ala
            420                 425                 430

Ala Met Lys Lys Lys Ile Tyr Ala Met Gly Gly Gly Ser Tyr Gly Lys
        435                 440                 445

Leu Phe Glu Ser Val Glu Cys Tyr Asp Pro Arg Thr Gln Gln Trp Thr
    450                 455                 460

Ala Ile Cys Pro Leu Lys Glu Arg Arg Phe Gly Ala Val Ala Cys Gly
465                 470                 475                 480

Val Ala Met Glu Leu Tyr Val Phe Gly Gly Val Arg Ser Arg Glu Asp
                485                 490                 495

Ala Gln Gly Ser Glu Met Val Thr Cys Lys Ser Glu Phe Tyr His Asp
            500                 505                 510

Glu Phe Lys Arg Trp Ile Tyr Leu Asn Asp Gln Asn Leu Cys Ile Pro
        515                 520                 525

Ala Ser Ser Ser Phe Val Tyr Gly Ala Val Pro Ile Gly Ala Ser Ile
```

```
                    530                 535                 540
Tyr Val Ile Gly Asp Leu Asp Thr Gly Thr Asn Tyr Asp Tyr Val Arg
545                 550                 555                 560

Glu Phe Lys Arg Ser Thr Gly Thr Trp His His Thr Lys Pro Leu Leu
                565                 570                 575

Pro Ser Asp Leu Arg Arg Thr Gly Cys Ala Ala Leu Arg Ile Ala Asn
                580                 585                 590

Cys Lys Leu Phe Arg Leu Gln Leu Gln Gln Gly Leu Phe Arg Ile Arg
                595                 600                 605

Val His Ser Pro
    610

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Gly Gly Ser Thr
1
```

GIGAXONIN FUSION PROTEIN AND METHODS FOR TREATING GIANT AXONAL NEUROPATHY

CROSS REFERENCE TO RELATED APPLICATIONS

This application claims priority to International Publication Number WO 2013/063309, filed on Oct. 25, 2012, which claims priority to U.S. Provisional Patent Application No. 61/550,940 filed on Oct. 25, 2011, the disclosures of which are hereby expressly incorporated by reference in their entireties.

INCORPORATION OF SEQUENCE LISTING

A paper copy of the Sequence Listing and a computer readable form of the Sequence Listing containing the file named "31377-71 (IURTC 12058)_ST25.txt", which is 13,070 bytes in size (as measured in MICROSOFT WINDOWS® EXPLORER), are provided herein and are herein incorporated by reference. This Sequence Listing consists of SEQ ID NOS: 1-11.

BACKGROUND OF THE DISCLOSURE

The present disclosure relates generally to fusion proteins for treating Giant Axonal Neuropathy (GAN). More particularly, the present disclosure is directed to fusion proteins including gigaxonin coupled to at least one cell penetrant peptide.

Giant Axonal Neuropathy (GAN) is an autosomal recessive disorder of the nervous system characterized by cytoskeletal disorganization. Patients suffering from GAN experience both peripheral and central nervous system manifestations including progressive polyneuropathy, ataxia, and seizures. Generally, these patients become bedridden early in life, and are not expected to live past the third decade of life.

The GAN gene encodes for gigaxonin, a 68 kDa protein which directs ubiquitin mediated proteolysis of cytoskeletal components. In the absence of gigaxonin, these proteins form cytoskeletal aggregates which result in distended and dysfunctional axons, particularly neuronal axons. This aggregate phenotype can be observed in other cells types, and aggregates of vimentin in fibroblasts have been defined in previous work to serve as a phenotypic marker for the disease state.

Because GAN is a single gene mutation disorder, it is a viable candidate for protein replacement therapeutics. Accordingly, there is a need in the art for treating GAN.

BRIEF DESCRIPTION OF THE DISCLOSURE

The present disclosure relates generally to fusion proteins including gigaxonin coupled to at least one cell penetrant peptide. These fusion proteins can be used to treat GAN in a subject in need thereof. In one embodiment, the fusion proteins can be administered to control at least one of Galectin-1 (GAL-1) levels and phosphorylated vimentin protein levels, thereby mediating aggregation of vimentin and the formation of vimentin-free zones in cells.

In one aspect, the present disclosure is directed to a fusion protein comprising gigaxonin coupled to at least one cell penetrant peptide.

In another aspect, the present disclosure is directed to a method of treating giant axonal neuropathy (GAN). The method comprises administering to a subject in need thereof a fusion protein comprising gigaxonin coupled to at least one cell penetrant peptide.

In another aspect, the present disclosure is directed to a method of reducing vimentin aggregation in vitro. The method comprises administering a fusion protein comprising gigaxonin coupled to at least one cell penetrant peptide.

In another aspect, the present disclosure is directed to a method of controlling Galectin-1 (GAL-1) levels. The method comprises administering to a subject in need thereof a fusion protein comprising gigaxonin coupled to at least one cell penetrant peptide.

In another aspect, the present disclosure is directed to a method of controlling phosphorylated vimentin protein levels. The method comprises administering to a subject in need thereof a fusion protein comprising gigaxonin coupled to at least one cell penetrant peptide.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1 is a Western blot of fibroblasts as analyzed in Example 1.

FIG. 12C is a graph depicting the P-Vimentin/Vimentin ratio in TAT-Giga fusion protein treated cells as analyzed in Example 4.

DETAILED DESCRIPTION OF THE DISCLOSURE

Figure 2A:
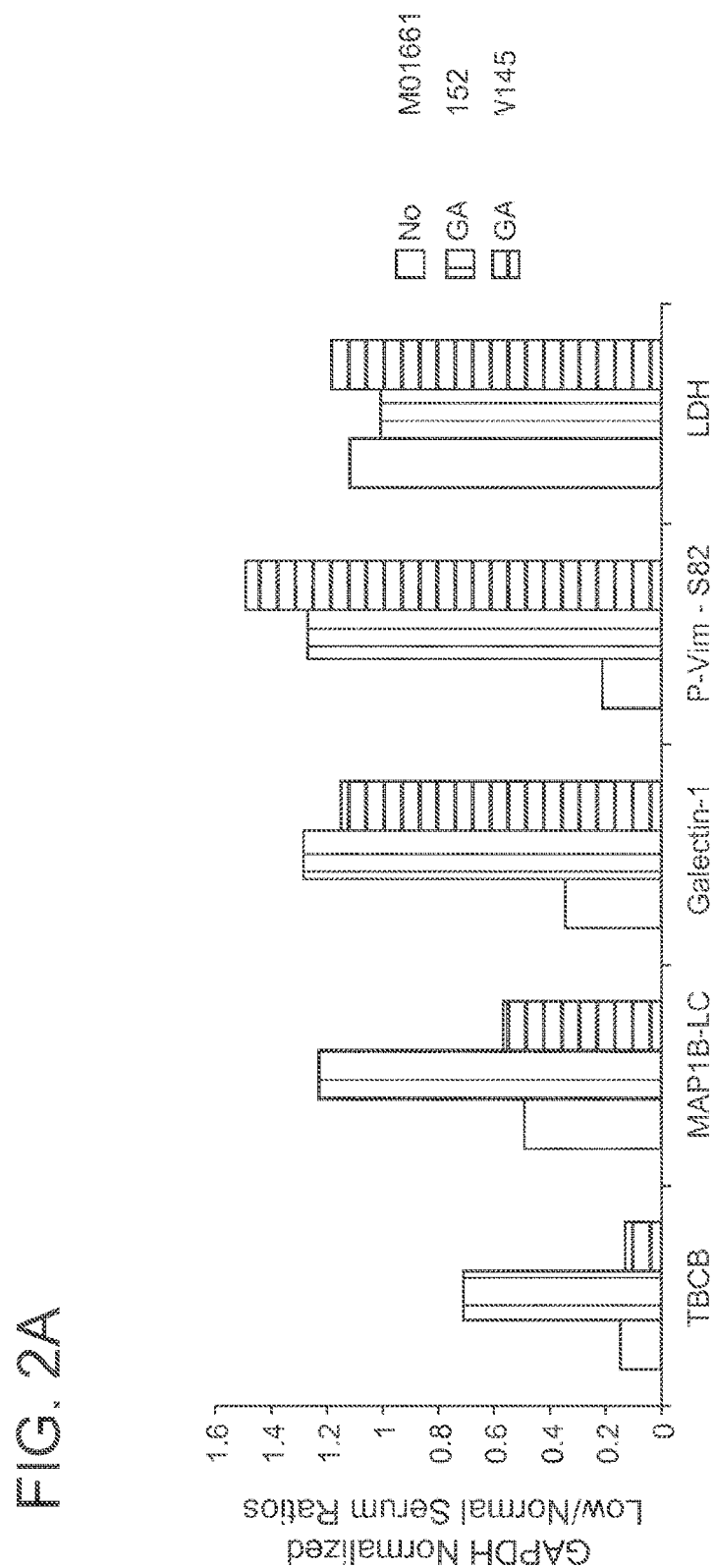
FIG. 2A is a graph depicting GAPDH normalized protein levels as analyzed in Example 1.

Unless defined otherwise, all technical and scientific terms used herein have the same meaning as commonly understood by one of ordinary skill in the an to which the disclosure belongs. Although any methods and materials similar to or equivalent to those described herein can be used in the practice or testing of the present disclosure, the preferred methods and materials are described below.

The terms "polypeptide" and "protein" are used interchangeably herein and indicate a molecular chain of amino acids linked through covalent and/or noncovalent bonds. The terms do not refer to a specific length of the product. Thus, peptides, oligopeptides and proteins are included within the definition of polypeptide. The terms include post-expression modifications of the polypeptide, for example, glycosylations, acetylations, phosphorylations and the like. In addition, protein fragments, analogs, mutated or variant proteins, fusion proteins and the like are included within the meaning of polypeptide.

The term "encoded by" as used herein refers to a nucleic acid sequence that codes for a polypeptide sequence. Also encompassed are polypeptide sequences that are immunologically identifiable with a polypeptide encoded by the sequence. Thus, a suitable "polypeptide," "protein," or "amino acid" sequence as used herein may be at least about 60% similar, at least about 70% similar, at least about 80% similar, at least about 90% similar, at least about 95% similar, at least about 96% similar, at least about 97% similar, at least about 98% similar, and at least about 99% or more similar to a particular polypeptide or amino acid sequence specified below.

The term "polynucleotide" as used herein refers to a polymeric form of nucleotides of any length, either ribonucleotides or deoxyribonucleotides. This term refers only to the primary structure of the molecule. Thus, the term includes double-stranded DNA and single-stranded DNA as well as double-stranded RNA and single-stranded RNA. The term as used herein also includes modifications, such as methylation or capping, and unmodified forms of the polynucleotide.

The term "coupled" is used herein to refer to linking, joining, attaching and fusing polypeptides together such that the polypeptides are part of a single, continuous chain of amino acids that does not occur in nature.

The terms "susceptible" and "at risk" as used herein, unless otherwise specified, mean having little resistance to a certain condition or disease, including being genetically predisposed, having a family history of and/or having symptoms of the condition or disease.

The terms "controlling" or "control" or "modulating" or "modulate" as used herein, unless otherwise specified, are used interchangeably to refer to the targeted movement of a selected Characteristic. Examples of controlling or control or modulating or modulate may be increasing protein levels or activity, decreasing or reducing protein levels or activity.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The present disclosure is directed to fusion proteins, and in particular, fusion proteins including gigaxonin coupled to at least one cell penetrant peptide, used in methods for treating Giant Axonal Neuropathy (GAN). More particularly, the fusion proteins are prepared by coupling gigaxonin with at least one cell penetrant peptide. The present methods include administering the Giga fusion proteins to a subject affected by GAN to control Galectin-1 (GAL-1) levels, to control phosphorylated vimentin protein levels, to reduce vimentin aggregation, and/or to prevent/reduce/control and/or treat malfunctions in the peripheral and central nervous system, thereby treating GAN. The methods may be useful in preventing GAN phenotypes, including progressive polyneuropathy, ataxia, and seizures.

These and other features of the proteins and methods, as well as some of the many optional variations and additions, are described in detail hereafter.

Gigaxonin (Giga) Fusion Proteins

The present disclosure is directed to Giga fusion proteins. The Giga fusion proteins include gigaxonin coupled to at least one cell penetrant peptide. As used herein, "a cell penetrant peptide" refers to peptides that result in the transport of gigaxonin across cell membranes. Particularly suitable cell penetrant peptides may be, for example, Transactivator of Transcription ("TAT"; SEQ ID NO: 1), protein transduction domain-4 (PTD-4; SEQ ID NO: 2), Pep-1 (SEQ ID NO: 3), transportan (SEQ ID NO: 4), antennapedia (SEQ ID NO: 5), VP22 (HSV-1 tegument protein; SEQ ID NO: 6), Cre ("41 kDa Cre recombinase peptide"), an arginine oligomer of D-arginine and L-arginine such as, for example, $R_7$ (SEQ ID NO: 7) and $R_9$ (SEQ ID NO: 8), and combinations thereof.

In some embodiments, the Giga fusion protein may further include at least one linker sequence. The linker sequence may be positioned between the gigaxonin peptide and the at least one cell penetrant peptide. Any amino acid sequence known to those skilled in the art may be used as the linker sequence so long as the linker sequence does not reduce, inhibit or otherwise interfere with functioning of the cell penetrant peptide and the gigaxonin of the Giga fusion protein. The linker sequence may include, for example, 1, 2, 3, 4, 5, 6, 7, 8, 9, 10 or more amino acids. A particularly suitable linker sequence may be, for example, SEQ ID NO: 11 (GGST).

In one embodiment, the Giga fusion proteins can be a recombinant protein in which a nucleic acid molecule encoding a cell penetrant peptide amino acid sequence is operably linked to a nucleic acid molecule encoding gigaxonin. The terms "recombinant polypeptide" or "recombinant protein", are used interchangeably herein to describe a polypeptide, which by virtue of its origin or manipulation, may not be associated with all or a portion of the polypeptide with which it is associated in nature and/or is linked to a polypeptide other than that to which it is linked in nature. A recombinant polypeptide or protein may not necessarily be translated from a designated nucleic acid sequence. For example, the recombinant polypeptide or protein may also be generated in any manner such as, for example, chemical synthesis or expression of a recombinant expression system. In some embodiments, the Giga fusion proteins may include multiple copies of a cell penetrant peptide. For example, a Giga-TAT fusion peptide may be cell penetrant peptide-cell penetrant peptide-Giga. In some embodiments, the Giga fusion protein may include a cell penetrant peptide located at either the amino- or carboxy-terminus of Giga or both the amino-terminus and the carboxy-terminus of Giga.

Gigaxonin (SEQ ID NO: 9), also known as kelch-like protein, is a member of the cytoskeletal BTB/ketch (Broad-Complex, Tramtrack and Bric a brac) repeat family. Gigaxonin plays a role in neurofilament architecture, thereby helping to define the shape and size of neurons essential for normal nerve function. More particularly, gigaxonin is a substrate adaptor for a multisubunit E3 ubiquitin-proteasome system, thereby controlling the degradation of multiple cytoskeletal binding proteins, such as for example, microtubule-associated protein 8 (MAP8), microtubule-associated protein 1B (MAP1B), tubulin-folding cofactor B (TBCB), and Galectin-1 (GAL-1). Mutations in the GAN gene, which encodes for the protein gigaxonin, result in Giant axonal neuropathy (GAN), a rare autosomal recessive neurological disorder that causes disorganization of neurofilments. More particularly, disorganization of the neurofilaments may cause a change in architecture in the axons, causing the failure in signal transmission, causing these "Giant" axons to be unable to properly transmit signals, and eventually deteriorate, resulting in a range of neurological anomalies. Early signs of the disorder often present in the peripheral nervous system, causing individuals with this disorder to have problems walking. Later, normal sensation, coordination, strength, and reflexes become affected. Hearing or vision problems may also occur. Abnormally kinky hair is characteristic of GAN, appearing in almost all cases. As the disorder progresses, the central nervous system becomes involved, which may cause a gradual decline in mental function, loss of control of body movement, and seizures.

In some embodiments, the Giga fusion proteins may further include pharmaceutically acceptable carriers. As used herein, the phrase "pharmaceutically acceptable" refers to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the subject.

Pharmaceutically acceptable carriers may be, for example, excipients, vehicles, diluents, and combinations thereof. For example, where the proteins are to be administered orally, they may be formulated in compositions as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These compositions can be prepared by conventional means, and, if desired, the active ingredient (i.e., Giga fusion protein) may be mixed with any conventional additive, such as an excipient, a binder, a disintegrating agent, a lubricant, a corrigent, a solubilizing agent, a suspension aid, an emulsifying agent, a coating agent and combinations thereof.

Methods of Treating Giant Axonal Neuropathy

Further, the present disclosure is directed to the use of Giga fusion proteins to control Galectin-1 (GAL-1) levels, to control phosphorylated vimentin protein levels, to control phosphorylated vimentin/vimentin ratios, to reduce vimentin aggregation, to reduce vimentin-free zones and/or to prevent/reduce/control and/or treat GAN. As used herein "treating" or "treatment of" GAN refers to the administration or application of a TAT-Giga fusion protein to a subject in need thereof to combat, ameliorate, relieve, reduce, prevent or care for GAN phenotypes, including preventing/reducing/treating malfunctions in the peripheral and central nervous system.

Treatment may be assessed by methods known to those skilled in the art. Suitable methods for assessing treatment may include, for example, physical examination of the subject to assess clinical features, assessing protein levels by Western blot analysis, ELISA, and immunofluorescence, assessing protein expression by Northern blot analysis to determine mRNA levels and combinations thereof.

GAL-1 protein levels are significantly increased in GAN fibroblasts. GAL-1 activity is critical in a signaling cascade that results in the phosphorylation of vimentin. Thus, the accumulation of GAL-1 in GAN cells leads to the subsequent hyperphosphorylation of vimentin. This hyperphosphorylation stops the polymerization of intermediate filaments, and causes the neurofilament disorganization observed in the disease phenotype. By controlling the degradation of GAL-1, gigaxonin regulates the phosphorylation and organization of vimentin, and thus the integrity of the cellular intermediate filament structure.

In subjects suffering from GAN, increased vimentin phosphorylation of neurofilaments in the axons appears as the axonal cytoskeleton matures. It is believed that vimentin phosphorylation can block polymerization and disassemble neurofilaments. Further, phosphorylation restricts association of intermediate neurofilaments with motor proteins. Accordingly, by controlling, and preferably decreasing, phosphorylated vimentin protein levels and phosphorylated vimentin/vimentin ratios, symptoms of GAN can be reduced.

Giga fusion proteins may be administered to a subset of subjects in need of controlling Galectin-1 (GAL-1) levels, controlling phosphorylated vimentin protein levels, controlling phosphorylated vimentin/vimentin ratios and/or treating GAN. Some subjects that are in specific need of controlling Galectin-1 (GAL-1) levels, controlling phosphorylated vimentin protein levels, and/or treating GAN may include humans who experience progressive polyneuropathy (humans susceptible to or at elevated risk of experiencing progressive polyneuropathy), humans who experience ataxia (humans susceptible to or at elevated risk of ataxia), humans who experience seizures (humans susceptible to or at elevated risk of seizures), and the like. Humans may be susceptible to or at elevated risk for experiencing progressive polyneuropathy, ataxia, and/or seizures due to heredity or other factors. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases or conditions. The terms "subject" and "patient" are used interchangeably herein.

Other suitable subjects may be experimental animals such as, for example, mice, rats, rats, pigs, dogs, sheep and non-human primates.

The Giga fusion proteins may be administered by any method known to those skilled in the art. Suitable methods for administering the fusion protein may be, for example, orally, injected (e.g., intravenously, intraperitoneally, intramuscularly, and subcutaneously), drop infusion preparations, ointments, drops, and the like. Proteins prepared as described herein may be administered in various forms, depending on the disorder to be treated and the age, condition, and body weight of the subject, as is well known in the art.

Giga fusion proteins may be administered as pharmaceutical compositions and pharmaceutically acceptable formulations that include pharmaceutically acceptable carriers as discussed herein.

Subjects are desirably administered from about 0.3 µg to about 1.5 µg of the Giga fusion protein.

The following examples illustrate specific embodiments within the scope of the present disclosure. The examples are provided for the purpose of illustration and are not to be construed as limitations of the present disclosure.

EXAMPLES

Example 1

In this Example, fibroblasts obtained from a patient afflicted with Giant Axonal Neuropathy (GAN) were analyzed for purported gigaxonin targets.

Specifically, GAN fibroblasts (GAN MW152 and GAN 10-W145) and normal fibroblasts (GM01661) were seeded in normal serum (10%) media for 24 hours. Cells were then changed to normal (10%) and low serum (0.1%) media and cultured for an additional 72 hours. Cells were then processed for Western blot analysis.

Figure 2B:
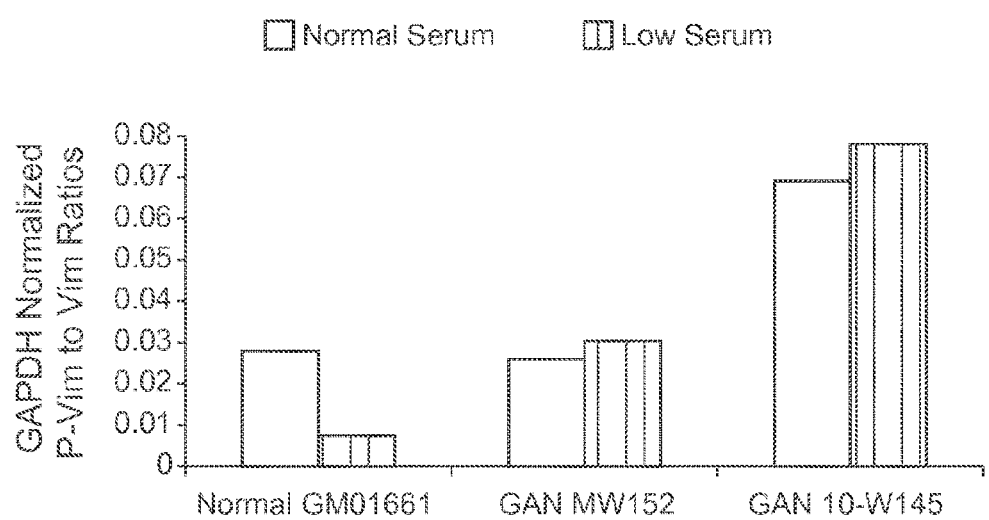
FIG. 2B is a graph depicting the ratio of phosphorylated vimentin to unphosphorylated vimentin for each cell type as analyzed in Example 1.

As shown in FIG. 1, gigaxonin was undetectable in GAN fibroblasts. Additionally, low serum conditions appeared to decrease the level of gigaxonin in normal fibroblasts. The effect of low serum media on other purported target proteins of gigaxonin varied (see, FIG. 1). Target protein levels were also normalized to GAPDH and graphed according to their low serum/normal serum ratios (FIG. 2A). Additionally, the ratio of phosphorylated vimentin (P-Vim) to unphosphorylated vimentin (Vim) in low and normal serum media of each cell type was graphed (FIG. 2B).

Cells cultured as described above were immunofluorescently stained for vimentin and tubulin to analyze the cytoskeletal structure in low serum and normal serum media.

Figure 3A:
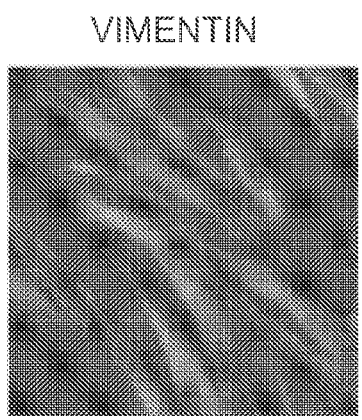
FIGS. 3A-3H are photographs of fibroblasts immunofluorescently stained for vimentin and tubulin as analyzed in Example 1.
Figure 3B:
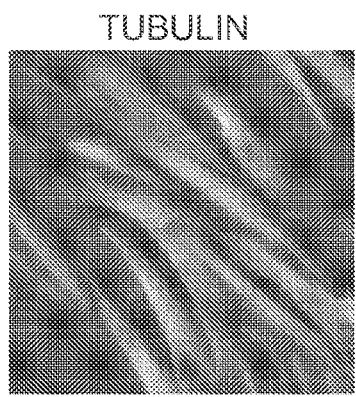
Figure 3C:
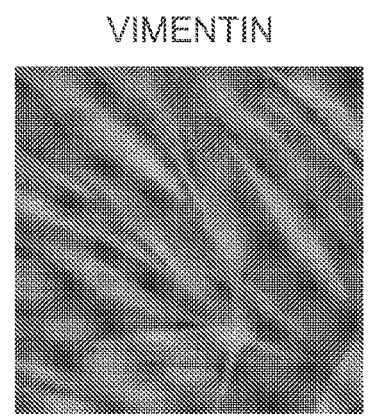
Figure 3D:
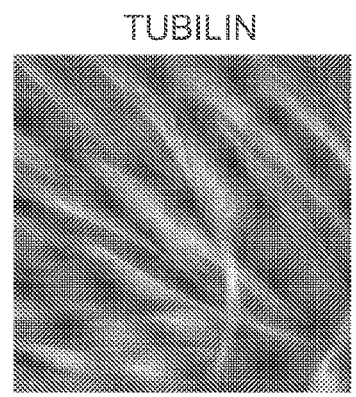
Figure 3E:
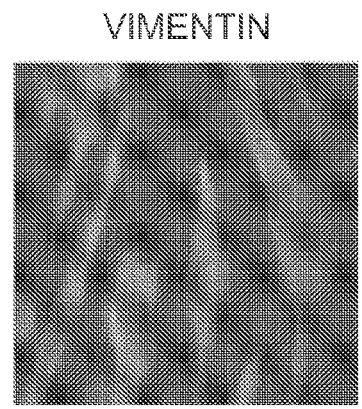
Figure 3G:
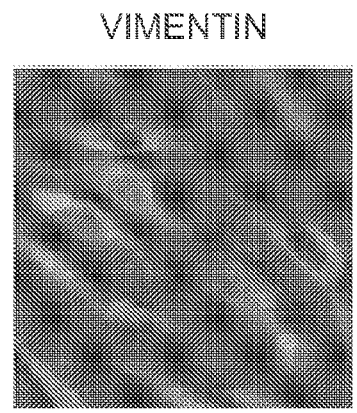
Figure 3F:
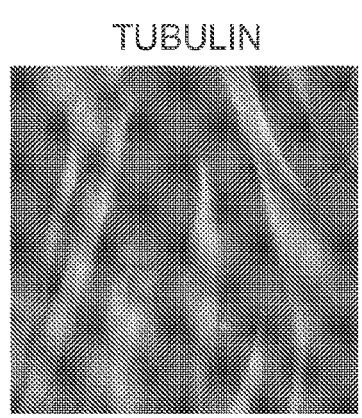
Figure 3H:
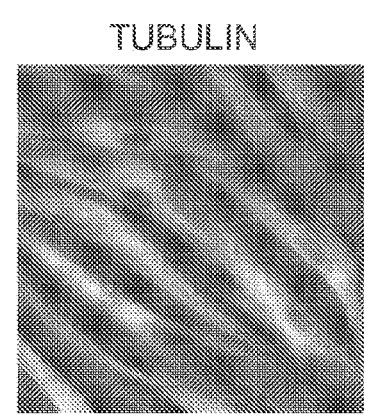

As shown in FIG. 3, normal fibroblasts cultured in both normal serum (FIG. 3A) and low serum (FIG. 3C) media contained normal vimentin intermediate filament and tubulin staining for microtubules (FIGS. 3B and 3D). GAN fibroblasts cultured in normal serum media also contained normal vimentin intermediate filament (FIG. 3E) and tubulin staining (FIG. 3F). GAN fibroblast cultured in low serum media, however, demonstrated the vimentin aggregate phenotype in which vimentin aggregates formed perinuclearly and left vimentin-free zones in the cell periphery (FIG. 3G). The low serum media specifically affected the intermediate filament cytoskeletal system, as tubulin staining for microtubules appeared normal (FIG. 3H).

Example 2

In this Example, the replacement of gigaxonin was used to determine the effect on the GAN phenotype in patient fibroblasts carrying the GAN mutation.

Specifically, the cell penetrant peptide, transactivator of transcription (TAT) was used to deliver human gigaxonin into diseased cells. A TAT-gigaxonin (TAT-Giga) fusion protein (SEQ ID NO: 10) was expressed and then purified from *E. coli*. The GAN phenotype was induced in fibroblasts from affected patients using low serum culture media. Cells were then treated with purified TAT-Giga fusion proteins. Cells were then assayed for the aggregate phenotype via immunofluorescence against vimentin and α-tubulin. Cells were imaged using confocal microscopy.

Figure 4A:
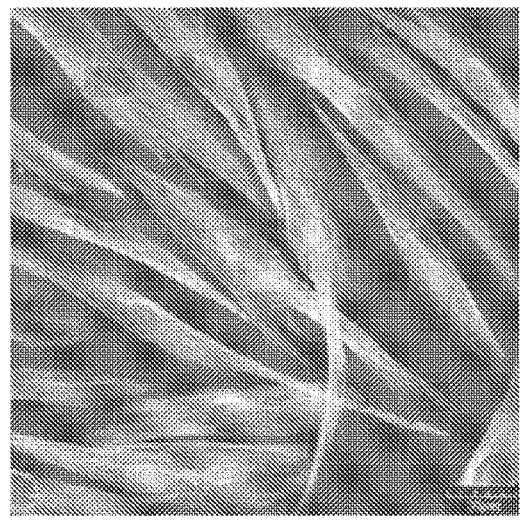
FIGS. 4A-4C are photographs of normal fibroblasts immunofluorescently stained for vimentin and α-tubulin as analyzed in Example 2.
Figure 4B:
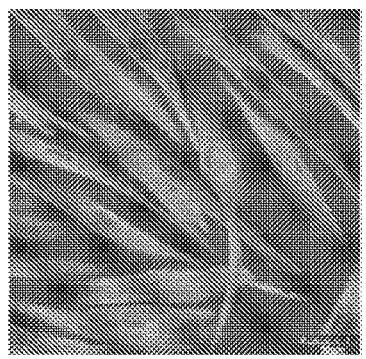
Figure 4C:
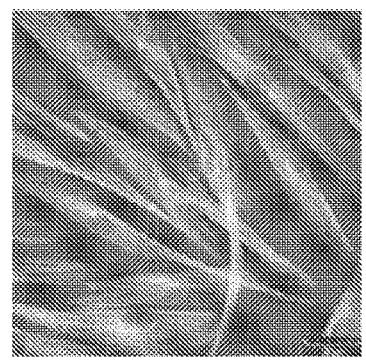
Figure 5A:
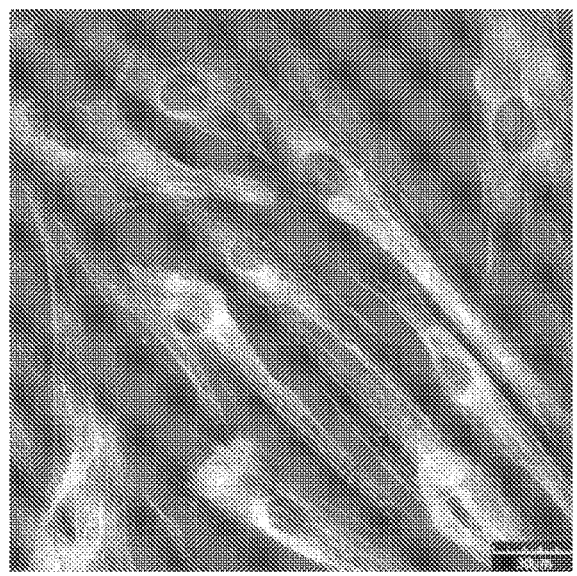
FIGS. 5A-5C are photographs of GAN fibroblasts immunofluorescently stained for vimentin and α-tubulin as analyzed in Example 2.
Figure 5B:
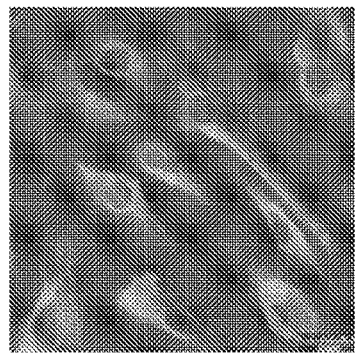
Figure 5C:
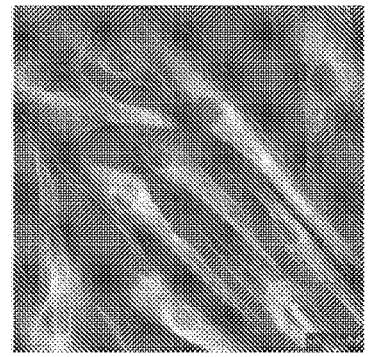
Figure 6A:
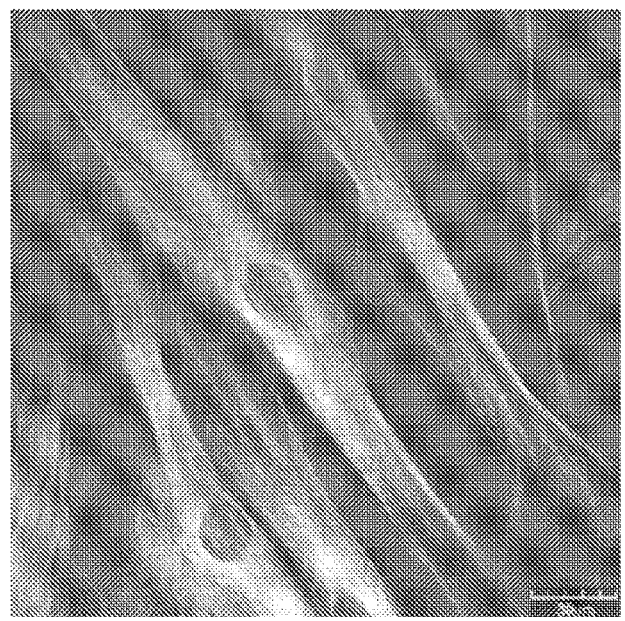
FIGS. 6A-6C are photographs of GAN fibroblasts treated with TAT-Giga fusion protein and immunofluorescently stained for vimentin and α-tubulin as analyzed in Example 2.
Figure 6B:
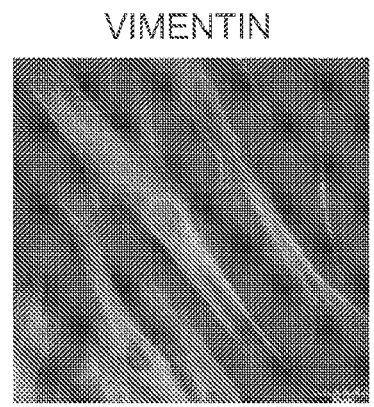
Figure 6C:
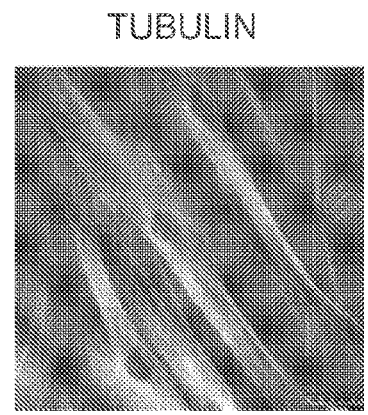

As shown in FIG. 4, normal fibroblasts stained for vimentin (FIG. 4B) and tubulin (FIG. 4C) exhibited a normal intermediate filament cytoskeleton and a normal microtubule cytoskeleton. An overlay image shows the co-localization of vimentin and tubulin staining (FIG. 4A). As shown in FIG. 5, GAN fibroblasts stained for vimentin (FIG. 5B) exhibited vimentin aggregates and vimentin-free zones in the cell periphery, whereas tubulin staining (FIG. 5C) showed a normal microtubule cytoskeleton. An overlay image (FIG. 5A) shows microtubule staining extending to the cell periphery in the vimentin-free zones, whereas vimentin staining remains aggregated near the cell nucleus. Significantly, GAN fibroblasts that were administered TAT-Giga fusion protein exhibited a normal intermediate filament cytoskeleton (as indicated by vimentin staining (FIG. 6B)) in which vimentin aggregates and vimentin-free zones failed to develop. Tubulin staining of these cells remained undisturbed (FIG. 6C). An overlay image (FIG. 6A) demonstrates the co-localization of the vimentin and tubulin staining similar to that observed in normal fibroblasts (see FIG. 4A).

Example 3

In this Example, the effect of administering TAT-Giga fusion protein on the formation of vimentin-free zones in GAN fibroblasts was determined.

GAN fibroblasts were cultured as described above. Cell were administered a low dose (0.3 µg) or high dose (1.5 µg) of TAT-Giga fusion protein. Both treated and untreated (control) fibroblasts were stained for vimentin and tubulin and assayed for number of vimentin aggregates.

Figure 7A:
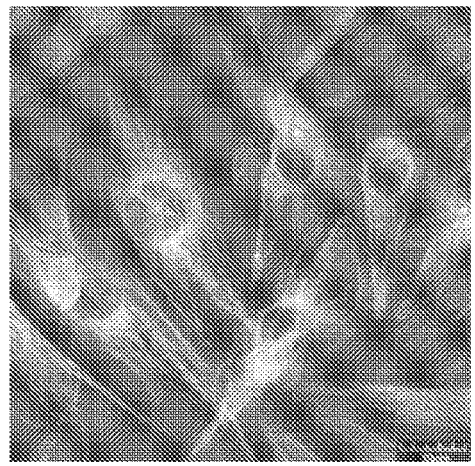
FIGS. 7A-7C are photographs of untreated GAN patient fibroblasts immunofluorescently stained for vimentin and tubulin as analyzed in Example 3.
Figure 7B:
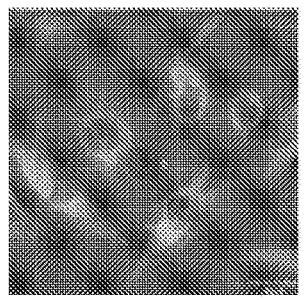
Figure 7C:
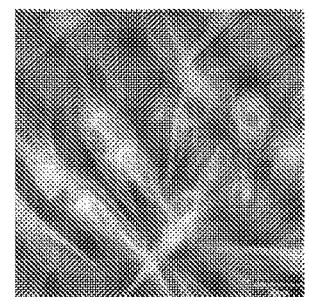
Figure 8A:
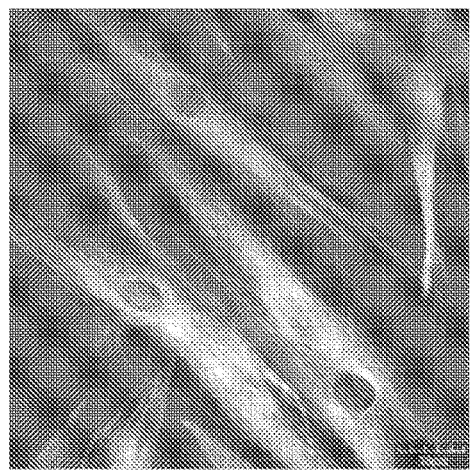
FIGS. 8A-8C are photographs of GAN patient fibroblasts treated with TAT-Giga fusion protein and immunofluorescently stained for vimentin and tubulin as analyzed in Example 3.
Figure 8B:
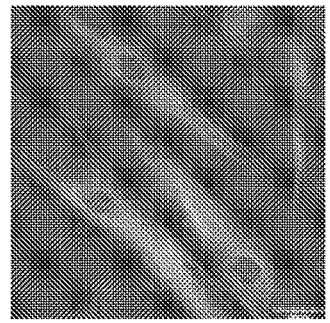
Figure 8C:
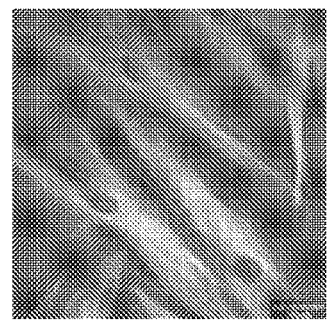

As shown in FIGS. 7A-C, staining of vimentin for intermediate filaments demonstrated the presence of peripheral vimentin-free zones in GAN fibroblasts (FIG. 7B), whereas microtubule staining (as revealed by tubulin staining; FIG. 7C) was normal. As shown in FIGS. 8A-C, staining of vimentin for intermediate filaments demonstrated that the administration of TAT-Giga fusion protein blocked the development of peripheral vimentin-free zones in GAN fibroblasts (FIG. 7B), whereas microtubule staining (as revealed by tubulin staining; FIG. 7C) was normal.

Figure 9:
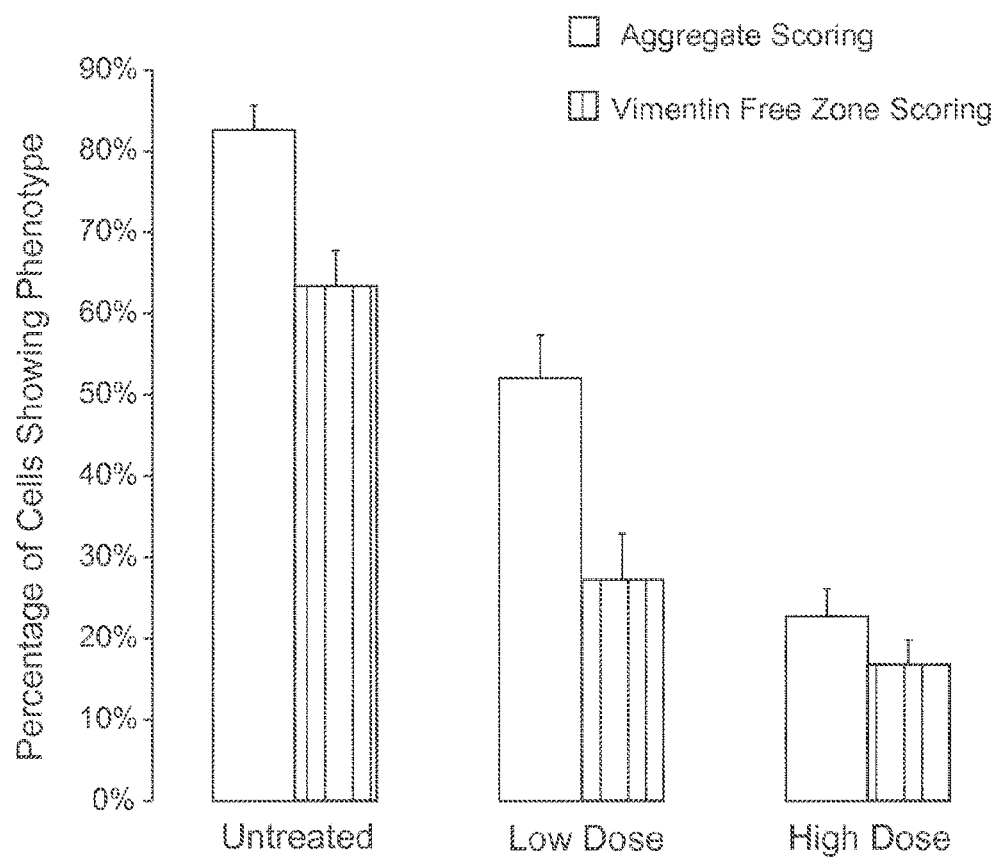
FIG. 9 is a graph depicting percentage of cells showing vimentin aggregate phenotype and vimentin-free zones as analyzed in Example 3.

As illustrated in FIG. 9, GAN fibroblasts treated with TAT-Giga fusion protein had significantly fewer aggregates and less intermediate filament cytoskeletal disorganization than control fibroblasts; 82.6% of control cells showed aggregates while only 22.7% of treated cells showed the aggregate phenotype. Further, this response was dose dependent to TAT-Giga fusion protein levels with 52% of cells showing aggregates at a lower protein concentration. These data indicate, based on morphology, that recombinant TAT-Giga fusion protein can prevent the GAN disease phenotype in affected fibroblasts.

Example 4

In this Example, the effect of administering TAT-Giga fusion protein on gigaxonin targets in GAN fibroblasts was determined.

GAN fibroblasts (MW152 and 10-W145) and normal fibroblasts (GM01661) were seeded in normal serum (10%) media. After 24 hours in culture, cells were changed to low serum (0.1%) media and TAT-Giga fusion protein was added. Phosphate buffered saline (PBS) was added for control cells. After 72 hours, cells were isolated and subjected to Western blot analysis.

Figure 10:
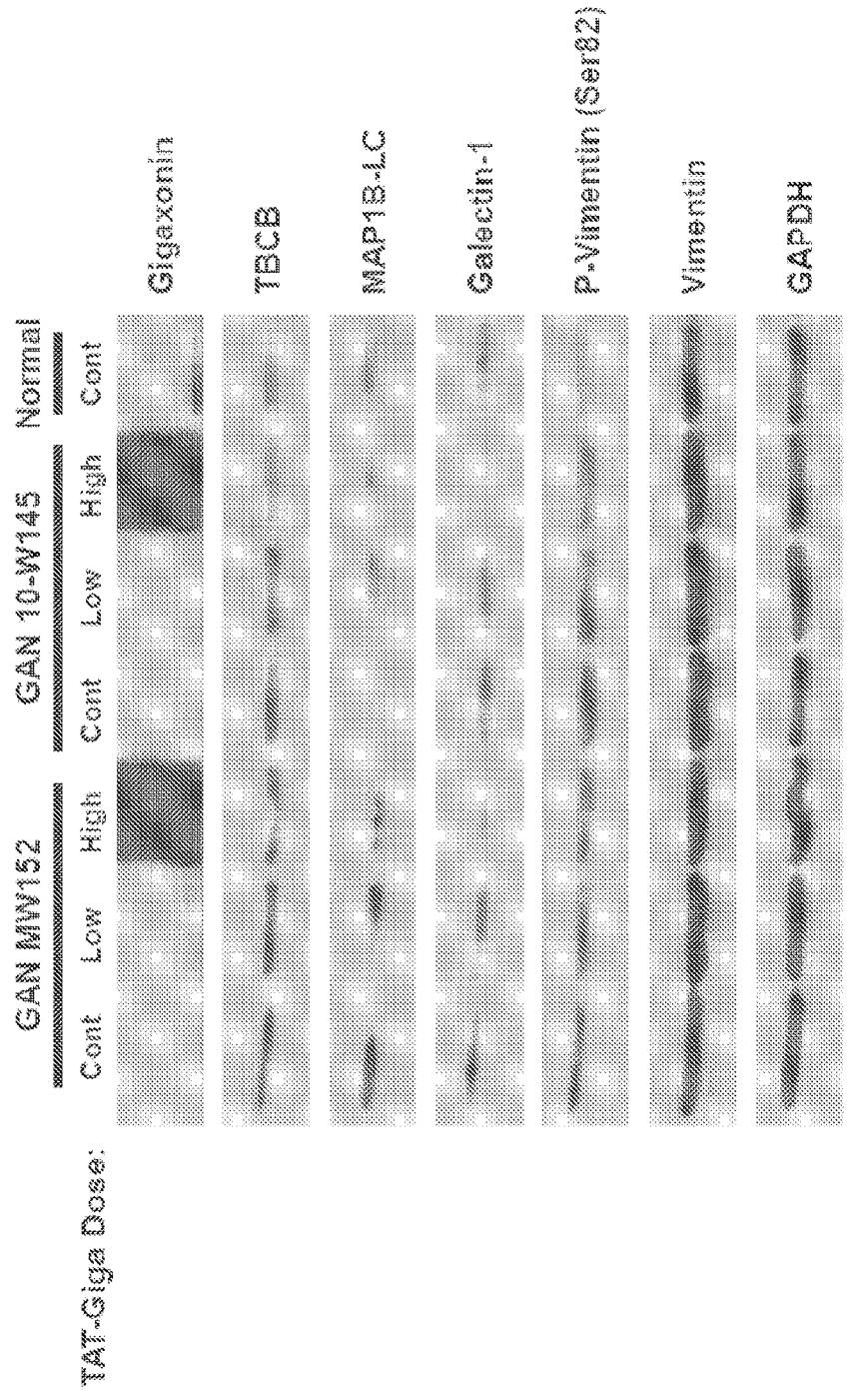
FIG. 10 is a Western blot of fibroblasts as analyzed in Example 4.
Figure 11A:
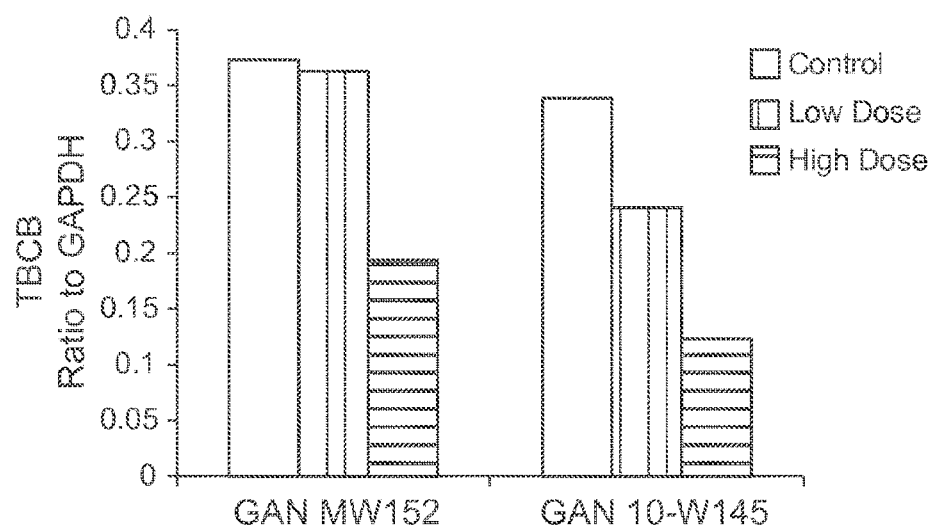
FIG. 11A is a graph depicting TBCB levels in TAT-Giga fusion protein treated cells as analyzed in Example 4.
Figure 11B:
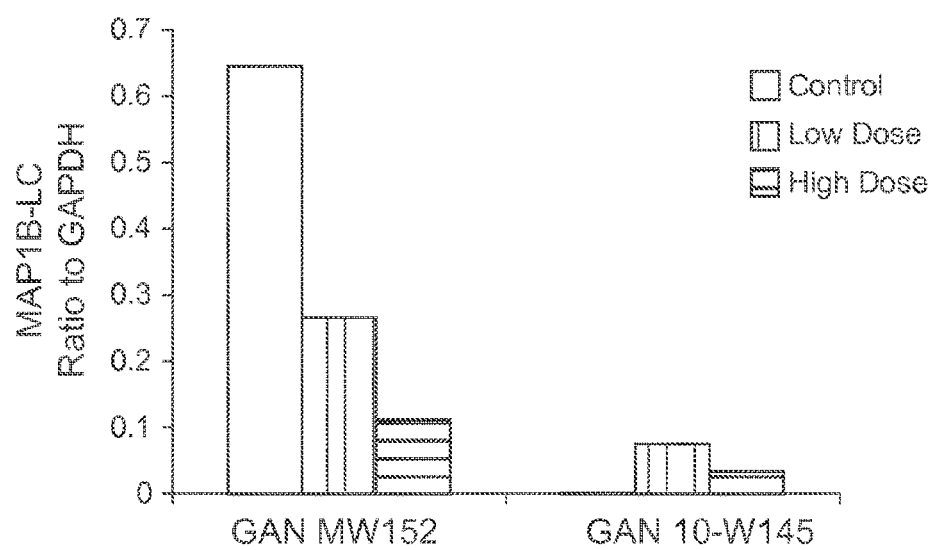
FIG. 11B is a graph depicting MAP1B-LC levels in TAT-Giga fusion protein treated cells as analyzed in Example 4.
Figure 12A:
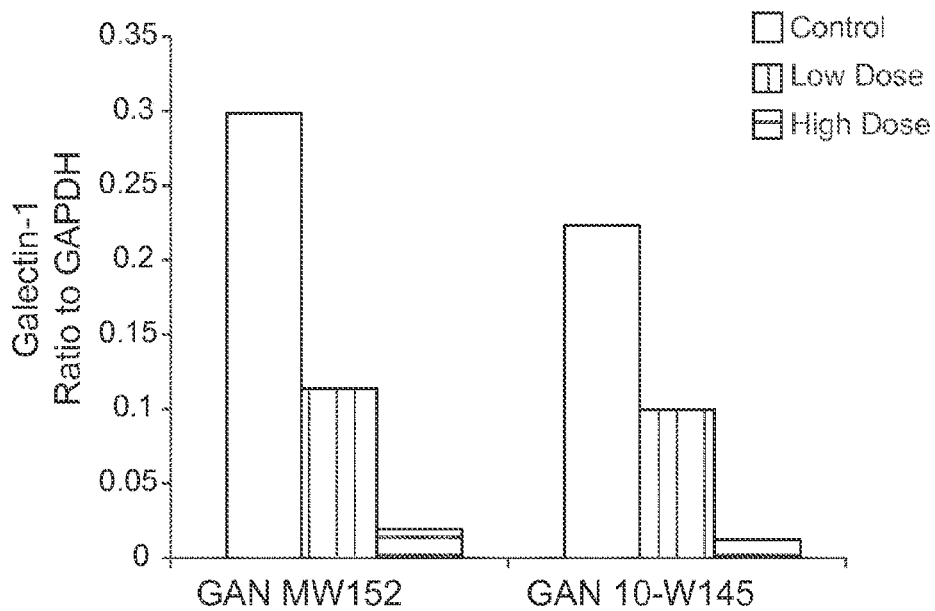
FIG. 12A is a graph depicting Galectin-1 levels in TAT-Giga fusion protein treated cells as analyzed in Example 4.
Figure 12B:
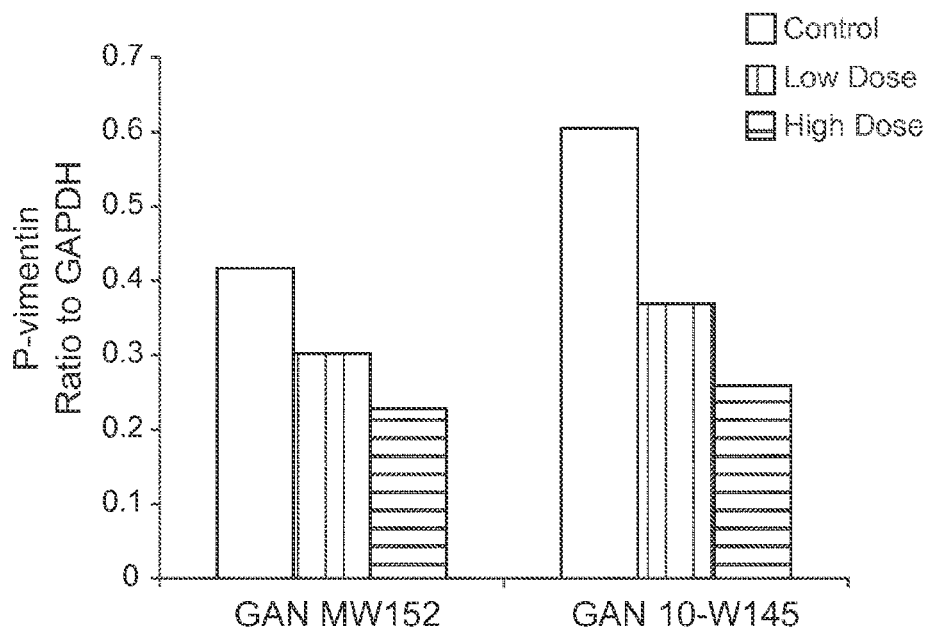
FIG. 12B is a graph depicting P-Vimentin (Ser82) levels in TAT-Giga fusion protein treated cells as analyzed in Example 4.

As shown in FIG. 10, TAT-Giga fusion protein administration into GAN fibroblasts resulted in a decrease in Galectin-1 (GAL-1), TBCB, MAP1B-LC and P-vimentin (phosphorylated vimentin) protein levels. As illustrated in FIG. 11A, TBCB levels in TAT-Giga fusion protein treated cells appeared to decrease in a dose-dependent manner in both GAN cell lines (MW152 and 10-W145). MAP1B-LC levels in TAT-Giga fusion protein treated cells appeared to decrease in a dose-dependent manner only in the GAN MW152 cell line (FIG. 11B). Protein levels of Galectin-1 decreased in a dose-dependent manner with TAT-Giga fusion protein administration (FIG. 12A), which corresponded to a decrease in P-vimentin (Ser82) level (FIG. 12B). As illustrated in FIG. 12C, the P-vimentin to vimentin (unphosphorylated vimentin) ratio decreased in a dose-dependent manner with TAT-Giga fusion protein administration.

Example 5

In this Example, the presence of gigaxonin on Galectin-1 (GAL-1) and phosphorylated vimentin levels in GAN fibroblasts was determined.

Normal (GM01661) fibroblasts and GAN MW152 cell line fibroblasts were cultured in normal ("Norm") and low serum media as described above. Cells were isolated and subjected to Western blot analysis.

Figure 13:
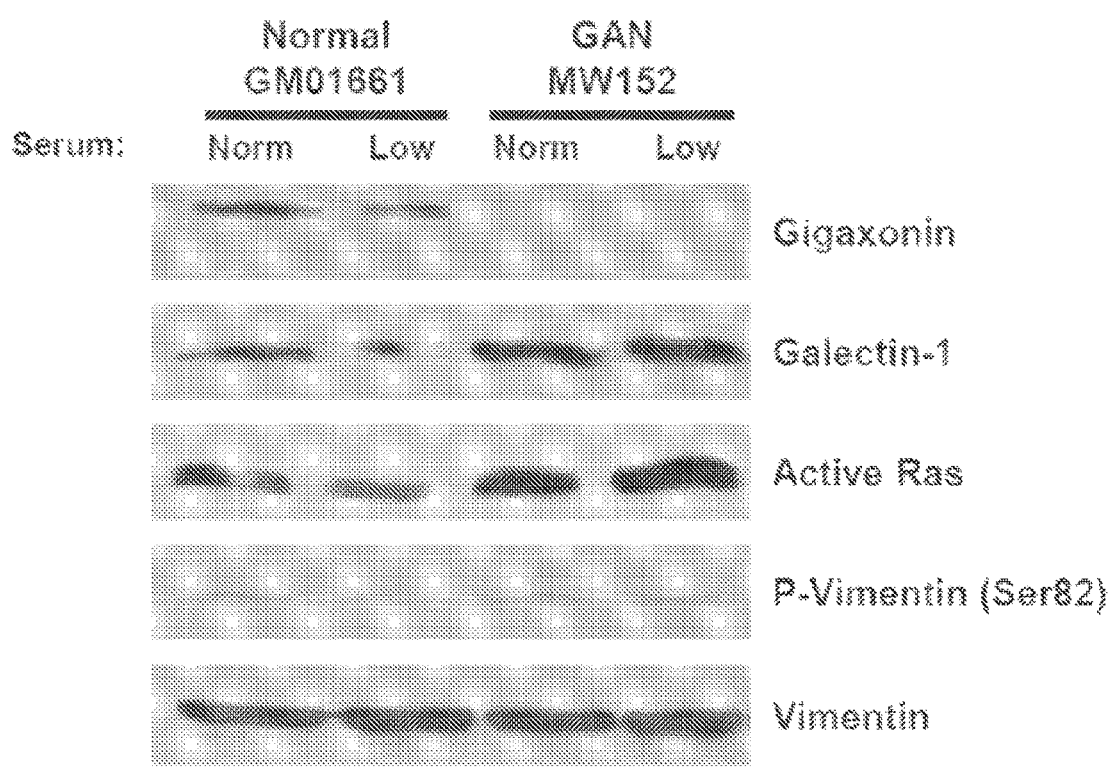
FIG. 13 is a Western blot of fibroblasts as analyzed in Example 5.
Figure 14A:
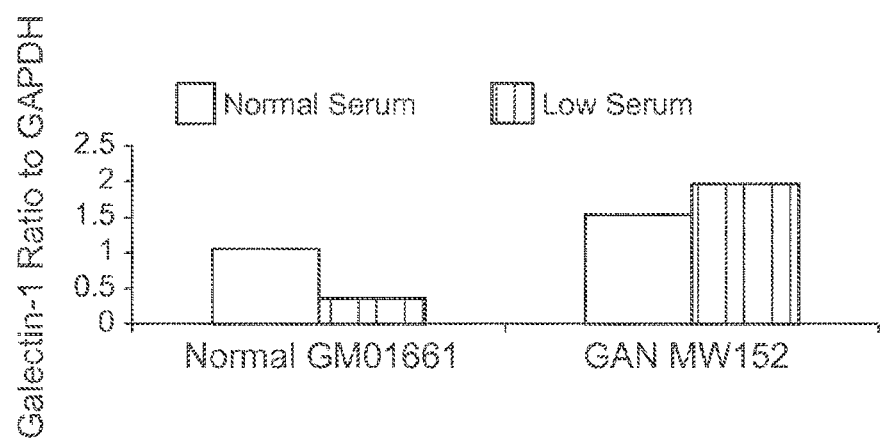
FIG. 14A is a graph depicting Galectin-1 (GAL-1) levels in fibroblasts as analyzed in Example 5.
Figure 14B:
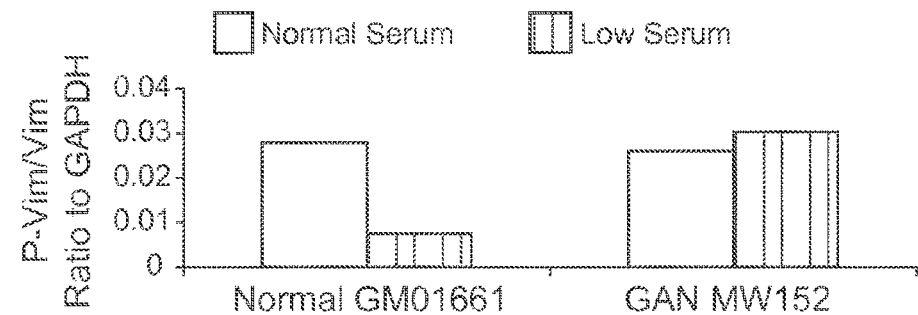
FIG. 14B is a graph depicting phosphorylated vimentin/vimentin ratios in fibroblasts as analyzed in Example 5.

As shown in FIG. 13, galectin-1 level was increased in the absence of gigaxonin in GAN MW152 fibroblasts (see also, FIG. 14A for GAL-1 levels). In normal (GM01661) fibroblasts cultured in normal serum. GAL-1 level was increased, which correlated with a higher P-Vim/Vim ratio (FIG. 14B). In normal (GM01661) fibroblasts cultured in low serum GAL-1 level decreased, which correlated with a lower P-Vim/Vim ratio (FIG. 14B).

These results demonstrate that gigaxonin regulates vimentin phosphorylation by controlling the degradation of GAL-1. In low serum condition and in the absence of gigaxonin, GAL-1 level increased, resulting in an increased P-Vim/Vim ratio and the formation of intermediate filament aggregates. Treatment of GAN fibroblasts with gigaxonin can block the formation of intermediate filament aggregates by activating the degradation of GAL-1. A decreased GAL-1 level results in a decreased P-Vim/Vim ratio, which allows intermediate filaments to polymerize properly, and thus blocks the formation of intermediate filament aggregates.

This written description uses examples to disclose the invention, including the best mode, and also to enable any person skilled in the art to practice the present disclosure, including making and using any proteins and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fusion protein comprising gigaxonin coupled to at least one cell penetrant peptide selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; an arginine oligomer; a 41 kDa Cre recombinase peptide; and combinations thereof.

2. The fusion protein of claim 1 further comprising a linker sequence.

3. The fusion protein of claim 1 being a recombinant protein.

4. The fusion protein of claim 1 being chemically synthesized.

5. The fusion protein of claim 1 further comprising a pharmaceutically acceptable carrier.

* * * * *